United States Patent [19]

Selmonosky

[11] Patent Number: 5,766,130
[45] Date of Patent: Jun. 16, 1998

[54] VASCULAR TESTING METHOD

[76] Inventor: Carlos A. Selmonosky, P.O. Box 568, Ellijay, Ga. 30540

[21] Appl. No.: 762,690

[22] Filed: Dec. 12, 1996

Related U.S. Application Data

[63] Continuation of Ser. No. 291,288, Aug. 16, 1994, abandoned.

[51] Int. Cl.$^6$ ........................................ A61B 5/02
[52] U.S. Cl. ........................ 600/485; 600/492; 600/501
[58] Field of Search ........................ 128/672, 677–683, 128/688, 685; 600/485, 490, 491, 492, 494, 500, 501

[56] References Cited

U.S. PATENT DOCUMENTS

| | | | |
|---|---|---|---|
| 4,144,879 | 3/1979 | Nakayama et al. | 128/680 |
| 4,178,918 | 12/1979 | Cornwell | 128/682 |
| 4,406,289 | 9/1983 | Wesseling et al. | 128/670 |
| 4,718,426 | 1/1988 | Russell | 128/679 |
| 4,726,382 | 2/1988 | Boehmer et al. | 128/667 |
| 4,800,892 | 1/1989 | Perry et al. | 128/677 |
| 5,048,533 | 9/1991 | Muz | 128/679 |
| 5,050,613 | 9/1991 | Newman et al. | 128/679 |
| 5,090,417 | 2/1992 | Mollan et al. | 128/694 |
| 5,103,833 | 4/1992 | Apple | 128/687 |
| 5,152,296 | 10/1992 | Simons | 128/670 |
| 5,172,697 | 12/1992 | Koven et al. | 128/679 |
| 5,218,966 | 6/1993 | Yamasawa | 128/677 |
| 5,301,675 | 4/1994 | Tomita | 128/677 |
| 5,464,019 | 11/1995 | Anderson et al. | 128/685 |
| 5,566,677 | 10/1996 | Raines et al. | 128/694 |

FOREIGN PATENT DOCUMENTS 2725625  12/1978  Germany .

OTHER PUBLICATIONS

Abstract entitled "Office Diagnosis of Thoracic Outlet Syndrome by Means of an Inexpensive Test," submitted to Georgia Chapter of American College of Surgeons on Apr. 2, 1993.

Abstract entitled "Digital Arteriopathies: A simple Classification and its Diagnosis by Digital Pneumatic Plethysmography and Thermography," presented to the Annual Meeting of the American College of Angiology on Oct. 11, 1990.

Abstract of Lecture entitled "Thermography and Digital Pneumatic Plethysmography. Comparison of their Usefulness in the Diagnosis of Reflex Sympatheic Dystrophy," presented to the Annual Meeting of the American Academy of Thermology on May 13, 1990.

Abstract published in the Reflex Sympathetic Dystrophy Syndrome Association Review, Summer, 1992.

Article entitled "Plethysmography: History and Recent Advances," published in Angiolog –The Journal of Vascular Diseases, Mar., 1987.

Product Literature for Vascular Recorder advertised by NewMed Corporation, 1991.

Product Literature for the Automated Vascular Testing Multilab 2000, advertised by Unetixs Incorporated, date unknown.

Product Literature for the Freedom V multilab product, advertised by Unetixs Incorporated, date unknown.

(List continued on next page.)

*Primary Examiner*—Lee S. Cohen
*Assistant Examiner*—Bryan K. Yarnell
*Attorney, Agent, or Firm*—Troutman Sanders LLP; Gerald R. Boss, Esq.

[57] ABSTRACT

The present invention relates to a method for vascular testing for diagnosing circulatory and secondary nervous disorders. The method allows a non-technical person to rapidly plot blood pressure and/or volumetric blood flow wave forms from a plurality of separate digits and/or extremities of a patient. The change in circumference of each body part correlates to the amount of blood flow through the body being measured. The wave form may then be analyzed by a physician for the purpose of identifying abnormalities or disorders in a patient.

5 Claims, 8 Drawing Sheets

OTHER PUBLICATIONS

Product Literature for the CVE/Parks Flo–Lab Integrated Computer System, advertised by CVE Systems, Inc., Dec. 26, 1992.

Product Literature for the Parks Miniature Vascular Lab IV VIP–PAK System, advertised by CVE Systems, Dec. 26, 1992.

Product Literature Catalog published by Parks Medical Electronics, Inc., 1988.

Product Literature for the IMEXLAB9000, IMEXLABPLV, and the IMEXLAB 3000DX, advertised by Imex Medical Systems, Inc., Oct. 1993.

Product Literature for Hokanson Plethysmographs advertised by Hokanson, Jan. 1993.

Product Literature for a Portable Air Plethysmograph advertised by HealthWatch–Life Sciences, Cambridge, date unknown.

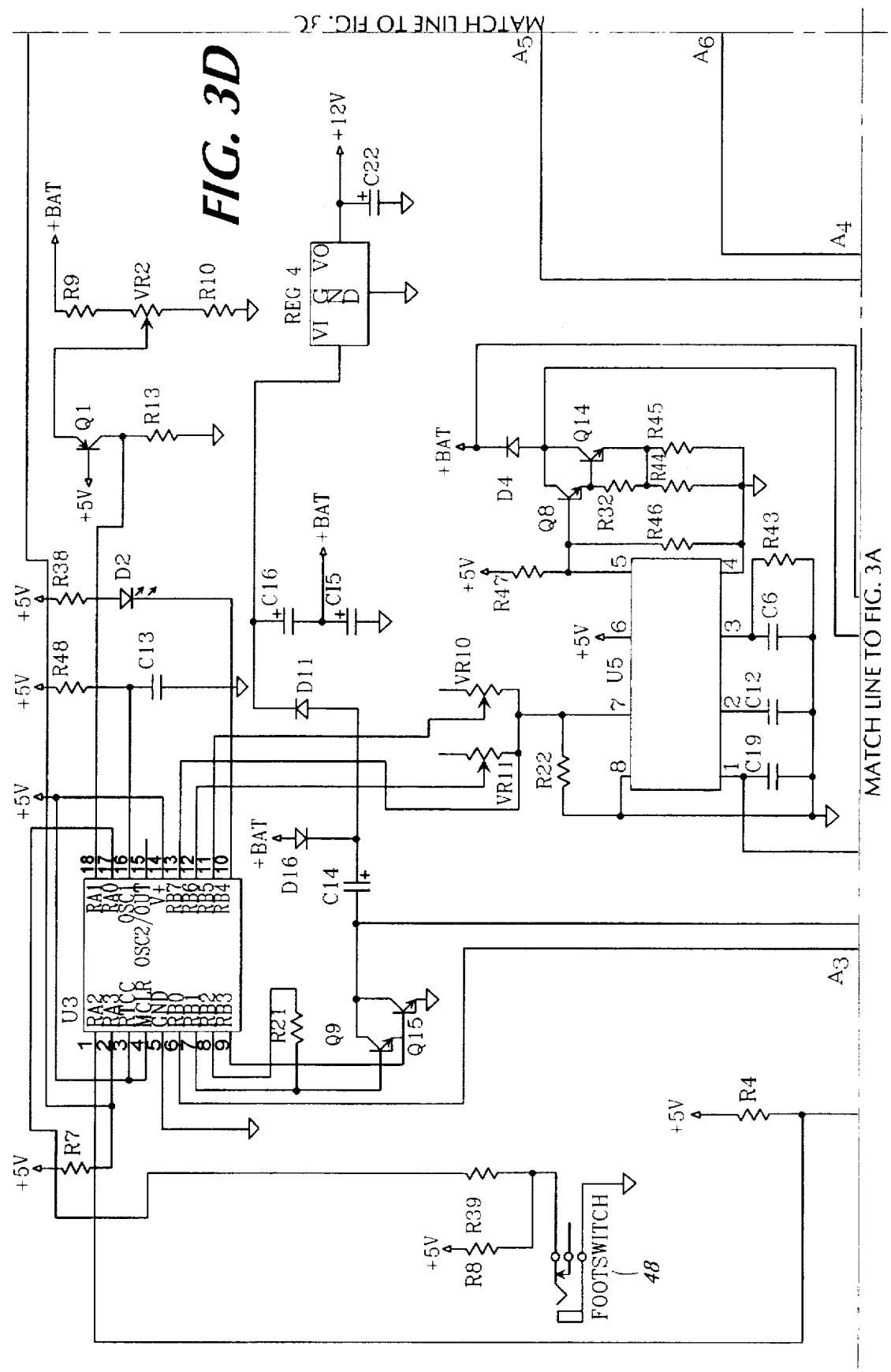

VASCULAR TESTING METHOD

This application is a continuation of application Ser. No. 08/291,288 filed on Aug. 16, 1994, now abandoned.

BACKGROUND OF THE INVENTION

1. Technical Field

This invention relates generally to a pressure measurement instrument, which measures volume changes within a specific volumetric domain with respect to time. More specifically, the present invention relates to a pneumoplethysmographic instrument, which detects circumferential changes over a specific length of digits or other extremities of a living organism by utilizing pneumatic sensing means.

2. Description of the Prior Art

Many devices utilize changes in air volume within a pneumatic cuff to measure various patient vital signs as a function of time. For example, U.S. Pat. No. 5,048,533 discloses a method and apparatus for examining the blood circulation of a living organism as a function of time using pneumatic cuffs placed on several limbs or digits. U.S. Pat. No. 5,152,296 discloses a device which continuously monitors blood pressure using a pair of finger cuffs having an electrocardiographic electrode and two radiation sources with sensor pairs. Finally, U.S. Pat. No. 4,406,289 also discloses a digital pneumatic cuff system for continuous blood pressure monitoring.

The above-referenced devices are often expensive and difficult to operate. Technicians who operate such instruments must be highly trained, and those instruments are often costly to repair and maintain. Furthermore, the above-referenced instruments have a limited number of pneumatic inputs, and are generally designed for monitoring a patient's vital signs over an extended period of time rather than diagnosing specific circulatory or nervous disorders.

Currently, a need exists for a device which may be specifically used to diagnose circulatory and secondary nervous disorders using pressure (e.g., plethysmographic) means. Furthermore, a need exists for such an instrument to be inexpensive and easy to maintain. Additionally, the instrument should be relatively easy to use so that a technician can properly perform testing procedures in a physician's office without extensive training on the techniques of using the instrument. Moreover, there is a need for a pressure measurement device which has multiple inputs, such as pneumatic inputs, so that circulatory parameters may be measured and rapidly and recorded from a great number of the patient's digits or limbs.

SUMMARY OF THE INVENTION

Generally speaking, the present invention relates to a pressure measurement device, such as a pneumoplethysmographic device. The pressure measurement device allows a non-technical person to rapidly plot blood pressure and/or volumetric blood flow wave forms from a plurality of separate digits and/or extremities of a patient. The change in circumference of each body part correlates to the amount of blood flow through the body being measured.

This change in volume is measured through the use of pressurized pneumatic cuffs which are wrapped and fitted around the particular extremity of interest. Ideally, the volumetric increase of the digit over the length of the cuff is equal to the decrease in volume of the cuff. If the amount of gas in the cuff remains constant, cuff pressure is then inversely proportional to the cuff volume. Therefore, cuff pressure is approximately proportional to volumetric blood flow through a particular digit. Cuff pressure may then be plotted as a function of time to create cuff pressure or volumetric blood flow curves or wave forms.

The primary usefulness of the recorded data of this instrument is the shape of the wave form created. The wave form shapes may then be analyzed by a physician for the purpose of identifying abnormalities in a patient's circulatory or nervous system.

More specifically, a single instrument according to the present invention comprises a plurality of pneumatic inputs for connection to separate pneumatic cuffs. Each of the pneumatic cuffs are adapted to fit over each of a patient's digits or other body extremities, and are pneumatically coupled to the main unit by appropriate means such as a neoprene tubing.

The main unit interfaces a pressure sensor to each of the pneumatic inputs with a transmitting means. Additionally, pneumatic valves are disposed between the pressure sensor and each of the pneumatic inputs. Switching means allows a technician to select a particular digit to be sensed by the pressure sensor. The pressure sensor converts the cuff pressure to an equivalent pressure signal which is appropriately processed. The processed signal is then fed to a display, such as a standard plotting recorder, where the cuff pressure signal as a function of time is plotted. Wave forms may then be produced which may be readily analyzed by a physician.

By having multiple pneumatic inputs, the amount of time needed to conduct a test on a patient with the inventive instrument is minimal for the following reason. Cuff pressure wave forms on all the fingers on one hand or other body extremities may be rapidly recorded for analysis by manual or automated switching between each pneumatic cuff secured to the patient digit. Therefore, the steps of releasing the cuff, fixing it to another digit or extremity, reinflating the cuff, and recording the cuff pressure wave forms are eliminated.

The present invention is operated in the following manner. First, a user, such as a technician or physician, connects each of the pneumatic inputs through pneumatic couplings (e.g., neoprene tubing) to appropriately sized pneumatic cuffs. The pneumatic cuffs may be placed on the patients fingers, wrists, upper arms, ankles, toes, penis or almost anywhere else, depending on the particular portions of the body which must be analyzed by the physician to properly examine the patient.

Each of the pneumatic inputs is pneumatically connected in parallel to a pressuring means, such as a manometer, by selecting an "ALL" position. The "ALL" position signals a solenoid valve in each of the pneumatic inputs to open so as to connect the pressuring means to each of the inputs. Each of the cuffs is then inflated to a specific pressure by the pressuring means. For example, when performing a digital analysis, the cuffs should be inflated to a pressure of approximately 40 mm Hg. If an analysis is being preformed on larger extremities, then the cuffs should be inflated to approximately 60 mm Hg.

After each of the cuffs has been pressurized, a specific pneumatic input may be selected. When a single input is chosen, the remaining solenoid valves to the other pneumatic cuffs are closed. At this point, the plotter within the main unit is activated by a convenient switching means, such as a footswitch or pedal, to generate the change in volume of the pneumatic cuff as a function of time, as sensed by the pressure sensor.

The signal generated by the pressure sensor is typically an analog signal which is fed to a galvanometer plotter having a multiple speed paper feeder. The user may adjust the gain of the cuff pressure signal to calibrate the height of the curve. Furthermore, the user may also adjust the center position of the plotter pen for a more convenient analysis of the cuff pressure wave forms generated by the plotter.

Once the plotter plots and records the first pneumatic input onto the paper, the next pneumatic cuff can then be rapidly chosen by the user and the above process repeated until a wave form for each extremity is plotted. The plotter paper may be advanced and removed from the unit for a detailed pressure wave form analysis on each digit or extremity measured by the user.

In another embodiment, the pressure from each pneumatic input is sensed simultaneously. Therefore, the signals generated from the pressure from each pneumatic input may be plotted at the same time.

The pulse volume curves obtained by the pressure measurement device according to the present invention may be analyzed for abnormalities to determine if the patient suffers from circulatory disorders, nervous disorders and many other disorders. For example, by analyzing the shape of the curves recorded by the inventive instrument and comparing the recorded curves to normalized curves generated by a healthy patient under an identical testing protocol, a physician may be able to pinpoint particular abnormalities in the blood flow of the patient. In turn, these may be related to specific diseases. Therefore, a multitude of arterial and nervous disorders may be rapidly diagnosed by comparing clinically recorded wave forms to "normal" characteristic wave forms which have been previously recorded from healthy patients.

For example, the present invention provides a simple method to detect early stages of Reflex Sympathetic Dystrophy (RSD). Early signs of RSD may be identified as a blunting of each wave peak within the cuff pressure wave form, a loss of the dicrotic notch between peaks, or a complete flattening of the entire wave form.

BRIEF DESCRIPTION OF THE DRAWINGS

The accompanying drawings illustrate the preferred embodiment of the invention, and serve to aid in the explanation of the principles of the invention.

FIGS. 3A–3D are schematic circuit diagrams of the pressure measurement device illustrated in FIG. 1, showing specific examples of the pressure sensor, pressure sensor signal processing means, pressure wave form plotting means, and overall instrument control means.

DETAILED DESCRIPTION OF PREFERRED EMBODIMENT

Figure 1:
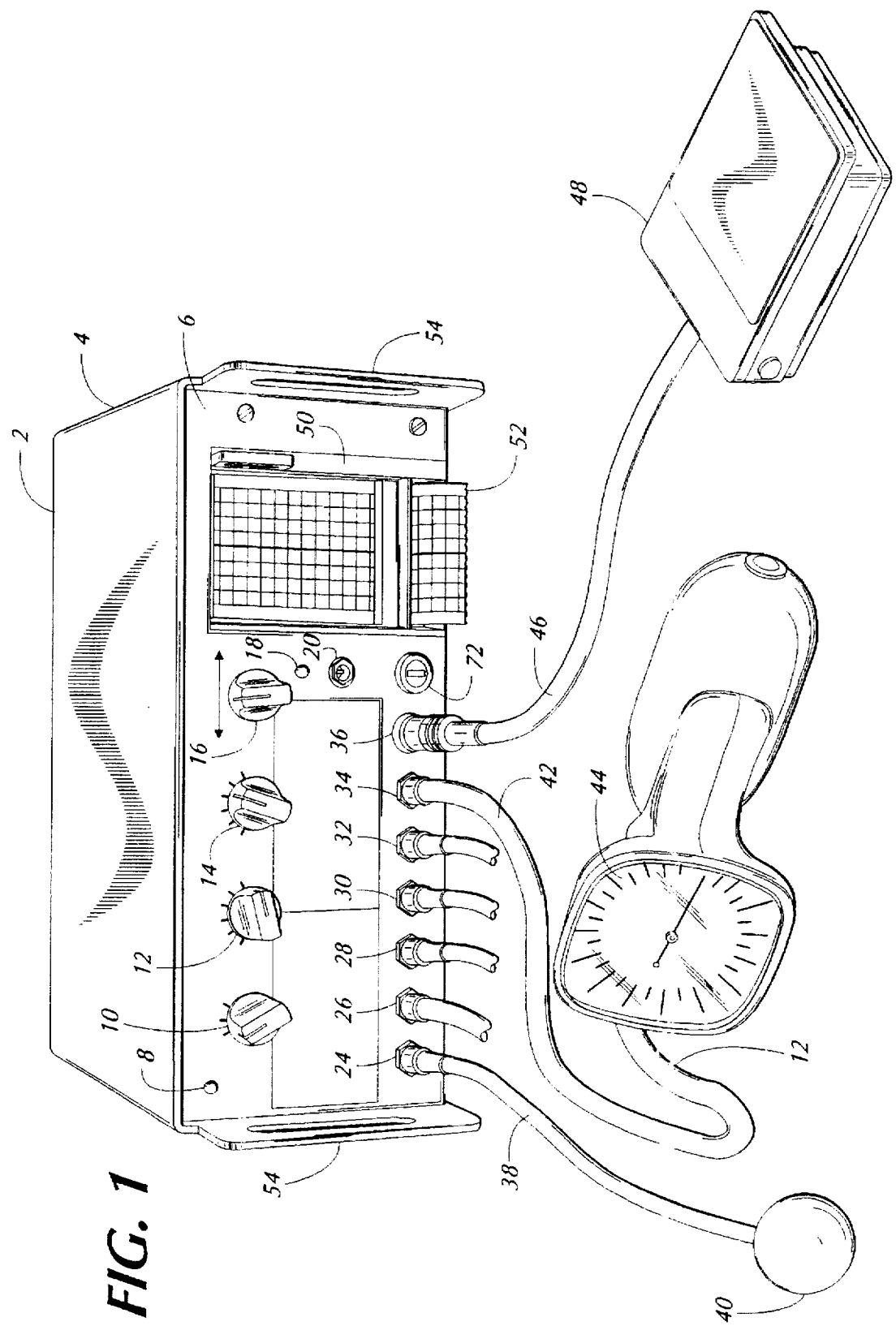
FIG. 1 is an perspective view of the pressure measurement device according to the present invention, illustrating the main unit which houses the electronics, five pneumatic inputs to the device, and a manometer used for inflating pneumatic cuffs coupled to the pneumatic inputs.

FIG. 1 illustrates a pressure measurement device such as a pneumoplethysmographic instrument according to the present invention, which is generally indicated by the numeral 2. The instrument is contained within a rugged housing 4 which may be formed from any suitable material such as steel, aluminum, or plastic. Housing 4 also includes carrying handles 54 disposed at a front portion thereof for allowing a user to carry the instrument into the field for remote patient examinations. Instrument 2 includes a face plate 6 which displays instructions for the use of the instrument and provides labels for a plurality of controls and indicators, as well as various interfaces for ancillary equipment used with instrument 2.

On a bottom portion of face plate 6, a plurality of pneumatic couplings 24, 26, 28, 30, and 32 are each connected to pneumatic cuffs 40 via tubing 38. Each of the cuffs 40 may be placed on any of the patient's extremities, such as any portion of the patient's limbs, fingers, or toes. Pneumatic coupling 34 interfaces a pressuring means, such as a manometer 44, to the instrument 2 via tubing 42. Tubing 42 may be made from any appropriate material, such as neoprene. Finally, pneumatic coupling 36 interfaces foot switch 48 with instrument 2 via tubing 46, such as neoprene. Footswitch 48 turns on the plotter or chart recorder 50 and also selects a paper feed speed, as will be discussed in greater detail below.

To facilitate portability and field work, instrument 2 is battery powered and may also include a recharging unit for the battery. At the left side of face plate 6, an indicator 8 flashes when the battery within the instrument 2 is low on power. Indicator 8 may be a standard light bulb, LED, or any other appropriate indicating means. Coupling 20 allows a charging device, such as a power pack, to be interfaced to instrument 2 for the purpose of charging the internal battery, and indicator 18 alerts the user when the battery is being charged. Indicator 18 may also be a standard light bulb, LED, or any other appropriate indicating means. Additionally, fuse 22 is also mounted on the face plate 6 for easy replacement. Fuse 22 protects the internal electronic components from being destroyed during a recharging phase and any other voltage surges.

Power switch knob 10 is disposed at a left portion of face plate 6. Power switch knob 10 is a three position switch, which may be moved from first "OFF" position to a second "ON" position to turn on the instrument. The third position on power switch knob 10 is a "PAPER FEED" selection which allows a user to advance the paper 52 from a display means, such as a chart recorder or plotter 50, so that the pressure wave forms may be conveniently analyzed.

Cuff select switch knob 12 is a switch having six positions. The first position on cuff select switch knob 12 is the select "ALL" position, which pneumatically and simultaneously connects each cuff coupled to the instrument to the standard manometer 44. When the "ALL" position is selected, the user may inflate each of the cuffs with the manometer 44 after they have been placed onto the patient. Of course, individual manometers 44 could be used for each individual cuff. Also, caps or an equivalent means may be used to shut off air pressure for unused cuffs or to deactivate the same. When the cuffs have been inflated to the appropriate pressure, individual cuffs may be isolated by selecting couplings 24, 26, 28, 30, or 32 by moving the switch 12 respectively to positions 1, 2, 3, 4, or 5 labeled on the face plate 6, to generate a separate pressure wave form for each cuff.

Gain select switch knob 14 allows the user to adjust the gain of the cuff pressure signal generated by the pressure sensor, as will be discussed in greater detail below. If a patient has been exercising rigorously, or has a very strong blood flow, then the technician may choose to lower the pressure sensor gain so that the pen in the plotter does not exceed a reasonable amplitude within the width of paper 52, which is preferably thermal paper, during a plotting phase. Similarly, if the patient is elderly or sedentary, the technician or physician may find it necessary to increase the cuff pressure signal gain, which widens the amplitude of the pressure wave form with respect to the width of paper 52. By adjusting the gain, the pressure wave forms are easier for the physician to analyze. However, the pressure wave forms for a same type of extremity of a patent should be recorded with the same gain. For example, all of the fingers of a patient should be analyzed with the same gain, while the legs should also be analyzed with the same gain, which may be different than the gain used for the fingers.

Finally, positioning switch knob 16 allows a user to adjust a position of the galvanometer pen within the plotter or chart recorder 50. This adjustment is useful for centering the wave form on the plotter paper 52.

Figure 2:
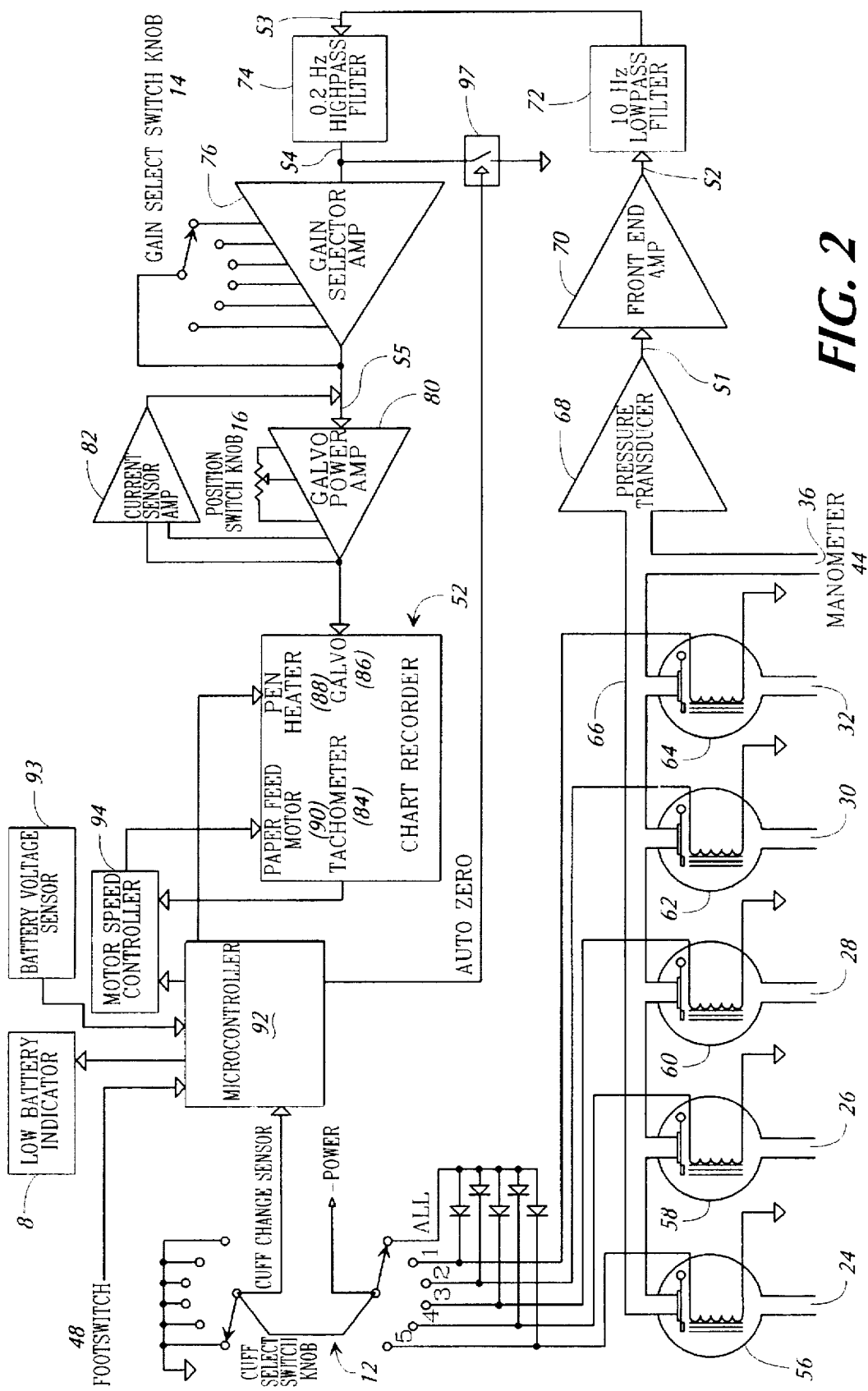
FIG. 2 illustrates functional circuit block diagram of the pressure measurement device illustrated in FIG. 1

FIG. 2 illustrates a block diagram representation of the electronic circuitry of the present invention. As illustrated, the cuff select switch knob 12 is shown as being in the position labeled "ALL." When the instrument power has been turned on, cuff select switch knob 12 powers solenoid air valves 56, 58, 60, 62, and 64 into open positions. Each solenoid valve then connects pneumatic couplers 24, 26, 28, 30, and 32 simultaneously though pneumatic connection 66 to the manometer 44 via pneumatic coupling 36. After each of the cuffs has been equally pressurized with respect to one another, by manometer 44, cuff select switch 12 may then be turned to cuff "1". In the position labeled "1", the solenoids 24, 26, 28, and 30 are deenergized by disconnecting them from power. Therefore, the connection between pneumatic connection 66 and their respective pneumatic couplings is closed. This leaves coupling 32 as pneumatically isolated with respect to the pressure transducer 68 for transmission of pressure from a cuff. Couplings 30, 28, 26, and 24 may be similarly isolated by choosing positions labeled "2", "3", "4", and "5", respectively on the cuff select switch knob 12.

The pressure transducer 68 produces an electrical signal, typically an analog signal, representative of the pressure from a cuff. The pressure transducer 68, which is preferably a four element bridge type sensor, is used as a pressure sensing means. Within the pressure transducer 68, a differential amplifier with a gain of 100 is used to bring the DC biasing offset signal S1 of the pressure transducer 68 from +4 volts to +2 volts. Signal S1 from the pressure transducer 68 is then processed by sending S1 to the front end amplifier 70, where the signal offset is adjusted and the signal S1 is further processed and amplified, creating signal S2.

Signal S2 is fed to a 10 Hertz low pass filter 72 where all signals above 10 Hertz are filtered out, processing and creating signal S3. Signal S3 is then fed to a 0.2 Hertz high pass filter 74, thus processing and creating a signal S4 having a bandwidth of 0.2 Hertz to 10 Hertz, or 0.4 Hertz to 7.0 Hertz with less than −3 db roll off at each end of bandwidth. Therefore, for the purposes of the galvanometer, 0.4 Hertz to 7.0 Hertz is the useful bandwidth.

Signal S4 is then amplified again in gain select amplifier 76. The gain select switch knob 14 is utilized to amplify or mitigate signal S4, thereby processing and creating signal S5.

There are 6 fixed gain settings calibrated for signal S5, where the following pressure changes will provide the following deflections on the paper 52:

1. 0.68 mm Hg (mercury) produces 1 cm deflection on paper 52;
2. 0.36 mm Hg produces 1 cm deflection on paper 52;
3. 0.21 mm Hg produces 1 cm deflection on paper 52;
4. 0.12 mm Hg produces 1 cm deflection on paper 52;
5. 0.044 mm Hg produces 1 cm deflection on paper 52; and
6. 0.011 mm Hg produces 1 cm deflection on paper 52.

Signal S5 is fed to galvanometer power amplifier 80. Since galvanometer 86 within chart recorder 52 has an impedance of about 32 ohms and requires a constant current drive to maintain a reasonably flat response curve, the galvanometer power amplifier 80 is differentially driven to obtain adequate voltage head room for displacing the galvanometer pen to its lower and upper limits throughout the bandwidth. A current sensor amplifier 82 provides negative feedback for the galvanometer power amplifier 80. A current sensor includes three (3) 11 ohm resistors connected in parallel for differentially amplifying the negative feedback. The galvanometer output drive signal S6 swings centered on 6 volts.

The chart recorder 52 includes the galvanometer 86 which moves a pen across the paper 54, a pen heater 88, a multiple speed paper feed motor 90, and a paper feed motor tachometer 84 for providing feedback for motor speed control. The microcontroller 92 controls the low battery indicator 8, pen heater 88, motor speed controller 94, and the auto zero switch 94.

When the instrument is first turned on, the pen heater, which is approximately 12 ohms, is turned on and stays on for about ¾ of a second using up 12 watts to quickly heat the pen heater up to the proper temperature. After this, the pen heater uses a pulse width modulated signal from the microcontroller 92 to control the pen instrument. The temperature is controlled by open loop modulating. When the paper feed motor is not running or is running at 5 mm/s, the power to the pen heater is approximately 1.5 watts. When the feed motor is running at 25 mm/s, the power increases to approximately 2 watts.

The paper feed motor 90 has a tachometer 84 attached to it. The tachometer 84 controls the speed of the paper feed motor 90 by providing feedback and is controlled by the microcontroller 92. There are three chart speeds controlled by the microcontroller 92. The first two speeds are 5 mm/s and 25 mm/s speeds. The third speed is the "paper feed speed," also referred to as the "full tilt" speed which is the fastest motor can go. Typically, the "full tilt" speed is 50 mm/s.

The footswitch controls the two slower speeds by using two modes of operation. The first mode is entered by pressing the footswitch such that the paper feed motor 90 runs at 5 mm/s. The second mode is entered by pressing the footswitch 48 then releasing it and pressing in again all within ¾ of a second. In the second mode, the paper feed motor 90 runs at 25 mm/s. Press and release the footswitch 48 again, and the motor returns to the first mode at a speed of 5 mm/s. Finally, if the footswitch 48 is pressed again, the paper feed motor 90 stops.

The auto zeroing switch 97 is for centering the waveform on the chart paper quickly and for resetting other circuitry when the instrument is activated or a new cuff is selected. The zero pulse lasts for ¾ of a second and is activated whenever the footswitch is pressed or whenever the cuff select switch changes position.

The battery is a 4 amp/hour lead acid type. The instrument uses about ¾ of an amp which gives the unit about 4½ hours of use before recharging is necessary. When the battery voltage sensor 93 senses voltage of approximately 11.2 volts, the power indicator 8 starts flashing. At this point, the instrument has about 20 minutes left before the instrument typically begins to malfunction. The instrument comes with a 1.1 amp 16 volt AC power pack charger wall transformer. The battery charger circuit is currently limited to ¾ of an amp making the charge cycle time about 6 hours. You cannot overcharge the battery and it is recommended that the instrument be kept on charge when not in use. Further, for safety reasons, the battery can only be charged when the power is off because the charger circuit is electrically disconnected from all other internal electronics when the power is on. It is not recommended that you use this instrument when the charger transformer is plugged into the wall.

The instrument 2 may be used to examine five digits (fingers, toes, etc.) by pneumatically attaching cuffs to pneumatic couplings 24, 26, 28, 30, or 32. If an examination utilizes two to four cuffs, the unused cuffs remain coupled to the instrument and inflated with cuffs which are placed on a patient, or the unused cuffs may be removed and caps may be placed over the unused pneumatic couplings. Furthermore, if only one cuff is needed for an examination, the unused cuffs may be kept on instrument 2 and inflated with the cuff being used, or the unused cuffs may be removed and the unused pneumatic couplings may be sealed with caps. Additionally, if only one cuff is chosen, then the cuff selector switch 12 may be turned to select that cuff without caps or cuffs on the remaining couplings, since the selector switch 12 will pneumatically connect the cuff being used directly to the manometer 44 and the pressure transducer 68.

Furthermore, if each of the cuffs are attached to the five fingers of the hand, blood flow to all the fingers more evenly than using one cuff. If only one cuff was used, the cuff would restrict the blood flowing through that finger a small amount, in turn, causing the blood to divert to the other fingers.

In another embodiment, the pressure from each cuff is sensed simultaneously. Therefore, the signals generated from the pressure from each pneumatic coupling 24, 26, 28, 30 and 32 may be plotted at the same time.

A schematic circuit diagram of a presently preferred but nevertheless illustrative embodiment of the present invention is shown in FIGS. 3A–3D.

Figure 3A:
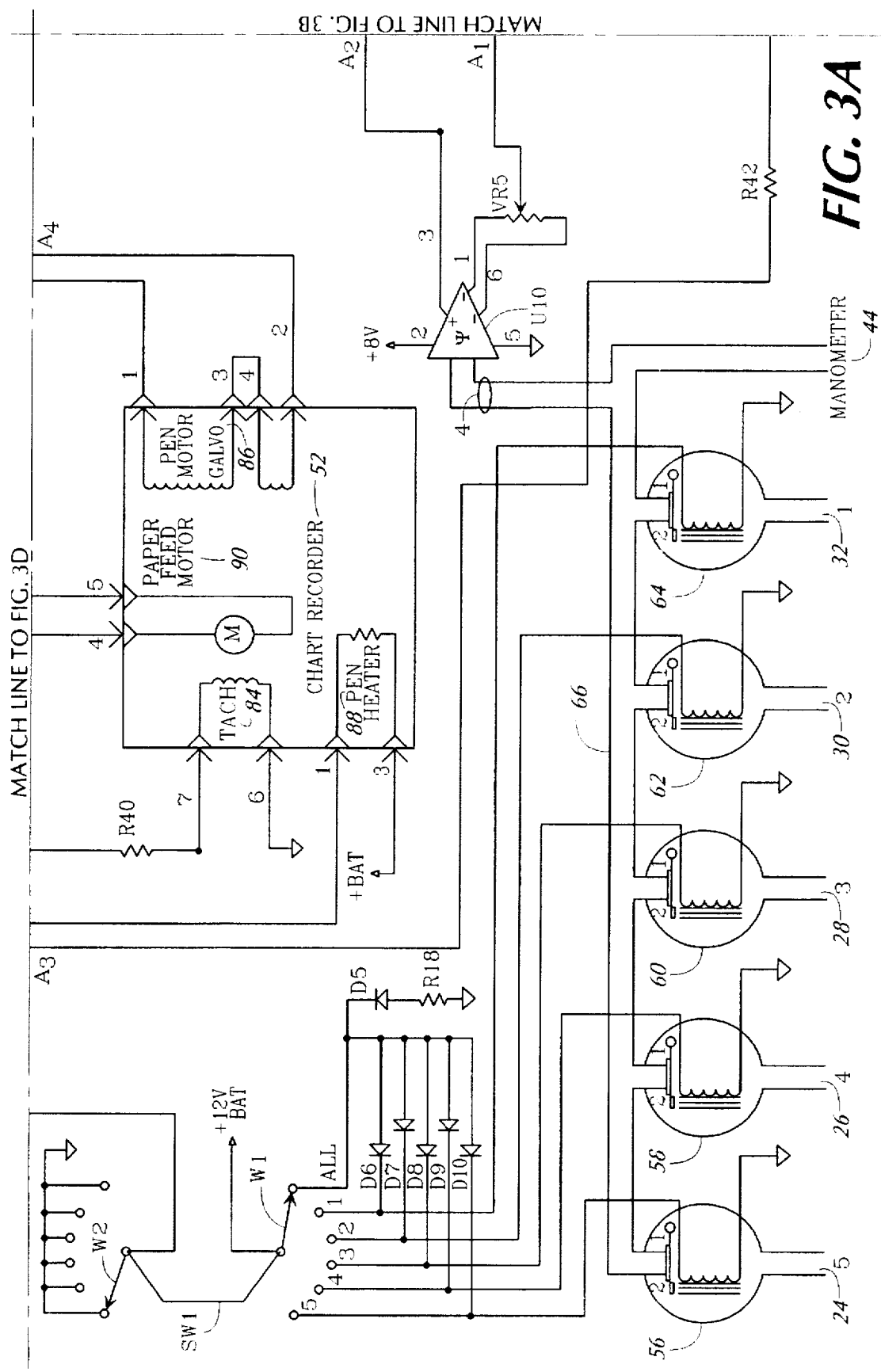

Referring to FIG. 3A, cuffs 1–5 are coupled to solenoid air valves 64, 62, 60, 58 and 56, respectively. Specifically, cuff 1 is coupled to solenoid air valve 64 with pneumatic coupler 32; cuff 2 is coupled to solenoid air valve 62 with pneumatic coupler 30; cuff 3 is coupled to solenoid air valve 60 with pneumatic coupler 28; cuff 4 is coupled to solenoid air valve 58 with pneumatic coupler 26; and cuff 5 is coupled to solenoid air valve 56 with pneumatic coupler 24.

The ground side of the coil for solenoid air valves 64, 62, 60, 58 and 56 is tied to ground. The power side of the coil of each of these solenoid air valves is connected to the cuff select switch SW1, a double pole six throw switch which is coupled to the cuff select switch knob 12 (FIG. 1). Specifically, the power side of the coil for solenoid air valve 64 is directly connected to the second position labeled "1" of the SW1 and connected through diode D6 to the first position labeled "ALL" of SW1. The power side of the coil for solenoid air valve 62 is directly connected to the third position labeled "2" of the SW1 and connected through diode D7 to the position labeled "ALL" of SW1. The power side of the coil for solenoid air valve 60 is directly connected to the fourth position labeled "3" of SW1 and connected through diode D8 to the first position labeled "ALL of SW1. The power side of the coil for solenoid air valve 58 is directly connected to the fifth position labeled "4" of the SW1 and connected through diode D9 to the first position labeled "ALL" of SW1. The power side of the coil for solenoid air valve 56 is connected to the sixth position labeled "5" of SW1 switch and connected through diode D10 to the first position labeled "ALL" of the SW1. The first position labeled "ALL" is also connected to diode D5, which is tied to ground through resistor R18.

Wiper W1 of SW1, which is used to switch between the "ALL," "1," "2," "3," "4," and "5" positions, is tied to the 12 volt battery. Wiper W2 of SW1 is coupled to the microcontroller U3 and to +5 volts through resistor R4 (FIG. 3D) but is normally grounded through the six positions corresponding to the six above-described positions. Therefore, when the cuff select knob 12 is turned to change a cuff selection and the wipers of SW1 change from position to position, a cuff a +5 volt (high) signal is momentarily sent to the microcontroller U3 to indicate the change in cuff selection.

The terminals of solenoid air valves 64, 62, 60, 58 and 56 are tied together such that each is coupled to the manometer 44 and input tube 4 of pressure transducer U10 of the pressure transducer circuit 68 (FIG. 2). Specifically, terminal 1 of solenoid air valve 64 is connected to the manometer 44; terminal 2 of solenoid air valve 64 is tied to terminal 1 of solenoid air valve 62; terminal 2 of solenoid air valve 62 is tied to terminal 1 of solenoid air valve 60; terminal 2 of solenoid air valve 60 is tied to terminal 1 of solenoid air valve 58; terminal 2 of solenoid air valve 58 is tied to terminal 1 of solenoid air valve 56; and terminal 2 of solenoid air valve 56 is connected to the input tube 4 of the pressure transducer U10 via pneumatic connection 66.

Figure 3B:
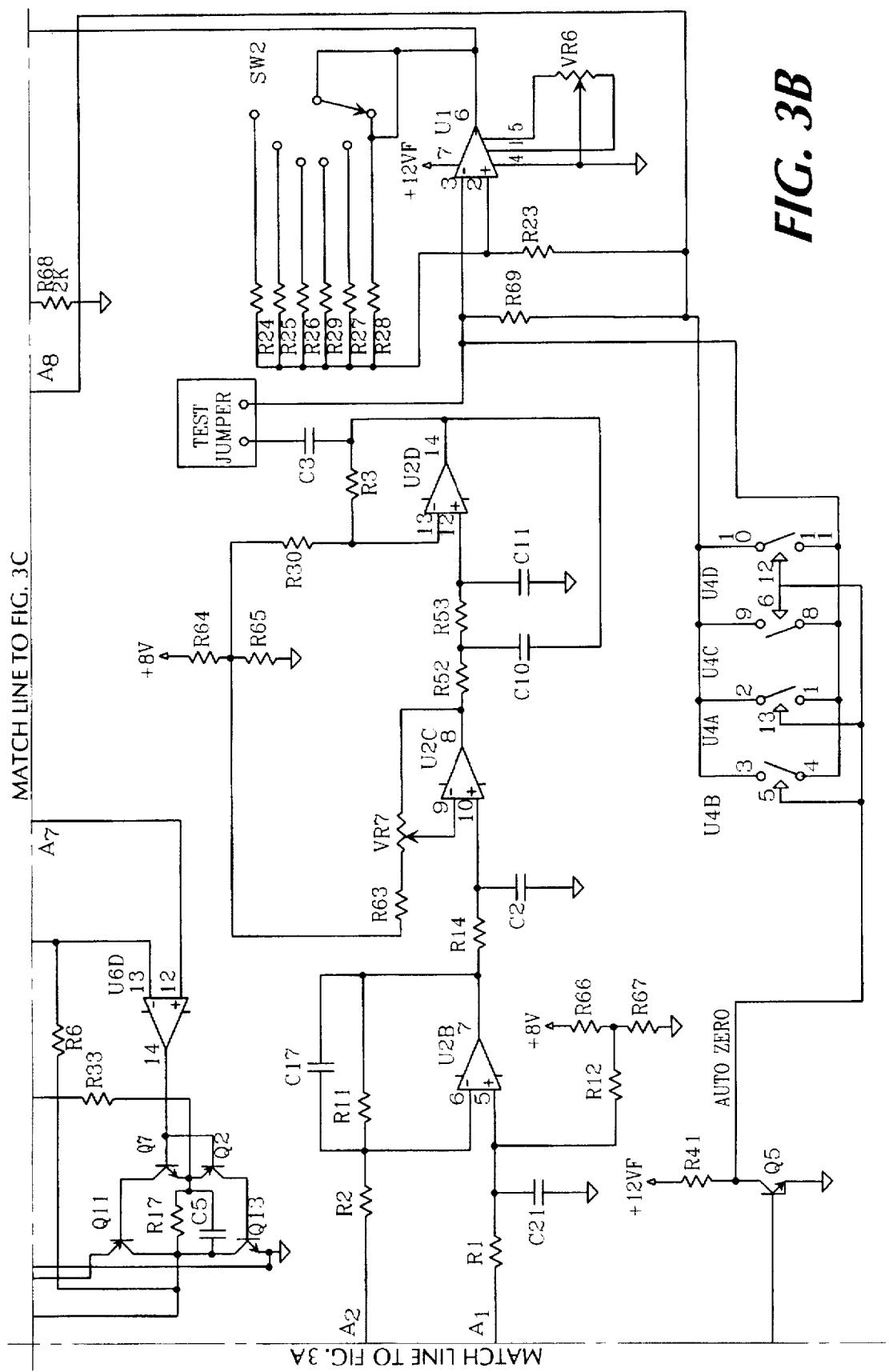

The pressure transducer U10 is connected to the manometer 44 via the input tube 4 of the pressure transducer U10. Pin 2 of the pressure transducer U10 is tied to +8 volts, while pin 5 is tied to ground. Potentiometer VR5 is connected across pins 1 and 6 (the "−" terminal) of VR5 and is used to adjust the offset from pressure transducer U10. Pin 3 (the "+" terminal) of pressure transducer U10 is connected to resistor R2 (FIG. 3B), and potentiometer VR5 is connected to resistor R1, which is tied to ground through capacitor C21 (FIG. 3B). R2, R1, and C21 offset the normal output of pressure transducer U1 and act as the front end gain of the front end amp 70 (FIG. 2) to obtain a gain of approximately 100 from differential amplifier U2B.

Referring to FIG. 3B, the R1 and C21 junction is connected to pin 5 (the "+" terminal) of U2B. Pin 5 of U2B is also connected to R12, which is tied to +8 volts through R66 and to ground through R67. R12, R66 and R67 form a resistor divider network, which is used to tweak the offset adjuster VR5 by bringing the DC biasing offset from the pressure transducer U10 from +4 volts to +2 volts.

Pin 6 (the "−" terminal) of U2B is connected to R2, as well as resistor R11 and capacitor C17 connected in parallel to pin 7 (the "output") of U2B. C17 and R11 form a single pole 16 Hertz filter to filter noise which would take up some of the dynamic range needed by differential amplifier U2B.

Pin 7 of U2B is connected to resistor R14, which is tied to ground through capacitor C2 and to pin 10 (the "+" terminal) of differential amplifier U2C, which is used to further tweak the gain from U2B. Pin 8 (the "output") of U2C is connected to resistor R52, which is connected to resistor R53 and capacitor C10, where R53 is tied to ground through capacitor C11. R14, C2, R52, C10, R53 and C1 form a three pole 10 Hertz low pass filter 72 (FIG. 2). The 10 Hertz filter limits the upper frequency response from pressure transducer U10 and calibrates the gain.

Also, connected to pin 8 of U2C is potentiometer VR7, which is tied to pin 9 (the "−" terminal) of U2C. VR7, which is connected to R63, is used to further adjust the gain. VR7 may be adjusted by checking the voltages at the Test Point connected between C10 and pin 14 (the "output") of differential amplifier U2D. For 0 MM/Hg, the voltage should be +2 volts, and for 100 MM/Hg, the voltage should be +8 volts.

R63 is connected to resistors R64, which is tied to +8 volts, and R65, which is tied to ground. R64 and R65 are used for biasing.

The R53 and C11 node is connected to pin 12 (the "+" terminal) of U2D, which is used to obtain sharper rolloff at the poles. Resistors R30 and R3, which are also attached to pin 14 (the "output") of U2D, are connected to pin 13 (the "−") terminal of U2D. R30 and R3 create feedback for U2D. Connected to R30 is the R64 and R65 node. Also connected to pin 14 of U2D is C10.

R3 is connected to capacitor C3, which is connected to the first terminal of the Test Jumper. The second terminal of the Test Jumper is connected to pin 3 (the "−" terminal) of gain selector amplifier U1, resistor R69 and the output terminal of switch SW4. C3 and R69 form a single pole high pass 0.2 Hertz filter 74 (FIG. 2). The Test Jumper is normally shorted. However, the Test Jumper is opened for adjusting the offset for U1 with potentiometer VR6 as discussed in more detail below.

Pin 2 (the "−" terminal) of U1 is connected to R23, as well as resistors R24, R25, R26, R27, R28 and R29, which are tied to a single pole six throw switch SW2. These resistors are tied across U1 to pin 6 (the "output") of U1 with SW2 to create varying feedback. Therefore, the gain select amp 76 (FIG. 2) operates by selecting the gain with the gain select switch knob 14 (FIG. 1), which switches the wiper of SW2 such that one of these resistors is connected across U1 to create the selected level of gain.

Connected across pins 1 and 5 of U1 is potentiometer VR6, which is used to adjust the offset of U1 when the Test Jumper is opened. Pin 4 of U1 is connected to the center pin of VR6 and ground, and pin 7 of U1 is tied to a +12 volts filtered.

Figure 3C:
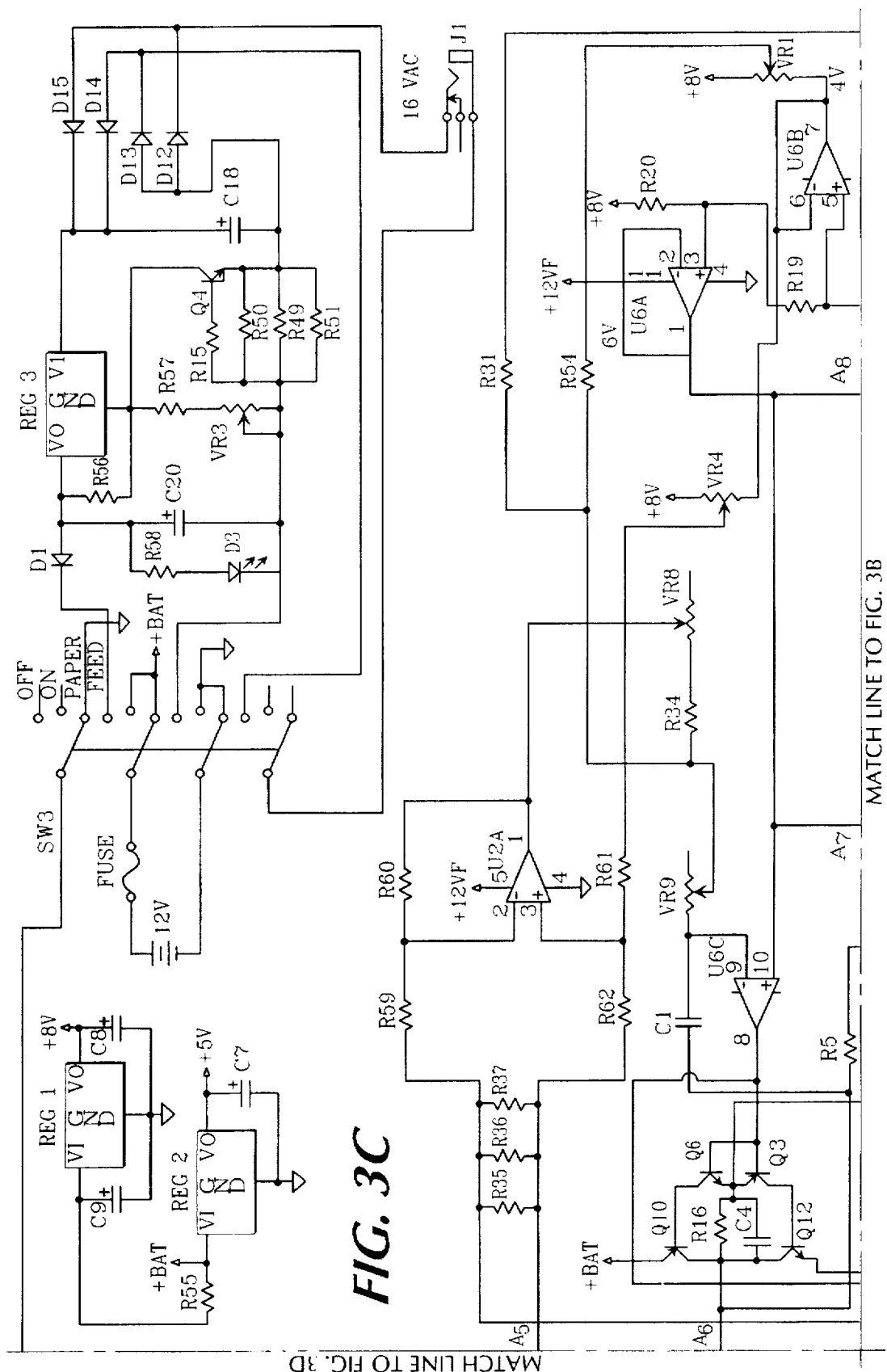

Referring to FIG. 3C, the output of U1 is connected to resistor R31, which is connected to resistor R54. Resistors R31 and R54 are input resistors to the pen positioning circuitry 16 (FIG. 2). R54 is connected to the center pin of VR1, which is connected to pin 7 (the "output") of differential amplifier U6B and to +8 volts. VR1 is coupled to positioning switch knob 16 (FIG. 1). Pin 6 (the "−" terminal) and the output of U6B are shorted together, and pin 5 (the "+" terminal) of U6B is tied to ground through resistor R68 (FIG. 3B). The "+" terminal of U6B is also connected to resistor R19, which is attached to pin 3 (the "+" terminal) of differential amplifier U6A and is coupled to +8 volts through resistor R20. U6B is used to generate the +4 volts pen positioning voltage.

Pin 2 (the "−" terminal) and pin 1 (the "output") of U6A are shorted together. Pin 1 of U6A is tied to +12 volts filtered, and pin 4 is tied to ground. U6A is used to generate the pen centering position of +6 volts, which centers the pen between 0 and +12 volts, the voltage supplied by the battery. Further, R20, R19, and R68 are used as resistor dividers for biasing the +6 volts created by U6A and the +4 volts created by U6B.

R31 is also connected to resistor R34, which acts as a feedback resistor to the galvo power amp 80 (FIG. 2), and to the center pin of potentiometer VR9, which is used to damp the frequency response of the galvo power amp 80 signal. R34 is also connected to the center pin of potentiometer VR8, which is used to trim the gain of the galvo power amp 80 signal.

VR9 is connected to pin 9 (the "−" terminal) of differential amplifier U6C and to capacitor C1, which is connected to resistor R5. Pin 10 (the "+" terminal) of U6C is connected to the pin 12 of (the "+" terminal) of differential amplifier U6D (FIG. 3B), and pin 8 (the "output") of U6C is connected to the base of transistors Q3 and Q6. Pin 13 (the "−" terminal) of U6D is connected to resistors R5 and R6, and pin 14 (the "output") of U6D is connected to the bases of transistors Q2 and Q7 (FIG. 3B). U6C and U6D and the corresponding circuitry are used as predrive circuitry for the galvo power amp 80 (FIG. 2), where U6C and U6D provide opposite swing polarities such that the peak-to-peak voltage for the galvo power amp 80 is +12 volts to −12 volts. Therefore, the predrive circuitry provides twice the +12 volts battery voltage for the galvo power amp 80. R5, R6 and C1 provide feedback for U6C and U6D.

The collector of Q6 is connected to the base of transistor Q10, and the emitter of Q6 is connected to the emitter of Q3, resistor R33 (FIG. 3B), and the node of resistor R16 and capacitor C4. The collector of Q3 is connected to the base of transistor Q12, and R33 is connected to the emitters of Q7 and Q2, as well as the node of resistor R17 and capacitor C5 (FIG. 3B). The collector of Q7 is connected to the base of transistor Q11, and the collector of Q2 is connected to the base of transistor Q13. The emitter of Q10 is connected to the +12 volt battery, pin 8 of U6C, and the emitter of Q11. The collector of Q10 is connected to R16, C4, R5 and the collector of Q12, and the emitter of Q12 is connected to the emitter of Q13 and ground. The collector of Q14 is connected to R17, C5, R6 and the collector of Q13 (FIG. 3B). The transistor circuitry composed of Q10, Q12, Q6, Q3, Q11, Q13, Q7 and Q2, as well as the corresponding circuitry, is used as a power driver for the galvo power amp 80 (FIG. 2). Q10, Q12, Q6, Q3 and corresponding circuitry compose a first power driver, and Q11, Q13, Q7 and Q2 form a second power driver which works oppositely to the first power driver. The combination of these two power drivers allows for double the power swing.

The R17, C5, R6 and the collector of Q13 are connected at a node, which is connected to a current sensor 82 (FIG. 2) for the galvo power amp 80 (FIG. 2). The current sensor 82 is composed of resistors R35, R36 and R37 connected in parallel. R17, C5, R6 and the collector Q13 node, as well as the current sensor 82, are also connected to resistor R59, which is part of a feedback loop for the galvo power amp 80. The other side of current sensors R35, R36 and R37 is attached to resistor R62, which is also part of the galvo power amp 80 feedback loop.

R59 is connected to resistor R60 and pin 2 (the "−" terminal) of differential amplifier U2A, and R62 is attached to resistor R61 and pin 3 (the "+" terminal) of U2A. Pin 1 (the "output") of U2A is connected to R60, pin 5 is attached to +12 volts filtered, and pin 4 is tied to ground. U2A is used to stabilize the feedback loop.

R61 is connected to the center pin of potentiometer VR4, which is connected to +8 volts and pins 6 and 7 of U6B. VR4 is used to tweak the offset of the gain for the feedback loop.

Referring back to FIG. 3A, the output from the galvo power amp circuit 80 is connected to the galvanometer 86 (FIG. 2), which is the motor that moves the pen across the plotting paper for the chart recorder 52 (FIG. 2). Specifically, the node connecting the current sensor network of R35, R36 and R37 to R62 (FIG. 3C) is attached to pin 1 of the galvanometer 86. Further, the node connecting the collectors of Q10 and Q12, R16, C4, C1 and R5 is connected to pin 2 of the galvanometer 86.

As described above, other components of the chart recorder 52 include the pen heater 88, paper feed motor 90 and tachometer 84 (FIG. 2). Referring to FIG. 3D, the pen heater 88 has pin 3 (FIG. 3A) connected to the +12 volt battery and pin 1 (FIG. 3A) connected to capacitor C14 and the collectors of transistors Q9 and Q15. The pen heater 88 is controlled by the microcontroller 92 (FIG. 2), which is composed of U3, through Q9 and Q15 coupled in a Darlington configuration. The base of Q15 is connected to the emitter of Q9 and to pin 9 (RB3) of U3, while the emitter of Q15 is tied to ground. RB3 generates a pulse width modulated signal for powering the pen heater 88. The base of Q9 is connected to pin 7 (RB1) of U3 and resistor R21, which is attached to pin 8 (RB2) of U3. R21 is used to limit the predrive current into the Darlington configuration of Q9 and Q15.

The paper feed motor 90 (FIG. 3A) is coupled to a driver circuit. Specifically, pin 4 of the paper feed motor 90 is connected to the collector of transistors Q8 and Q14, as well as the tail of diode D4, while pin 5 is connected to the +12 volt battery and the head of diode D4 (FIG. 3D). The base of Q14 is connected to the emitter of Q8 and resistor R32, while the emitter of Q14 is attached to resistors R32. The emitter of Q14 is also tied to ground through resistors R44 and R45. The base of Q8 is connected to resistor R46, which is tied to ground, and R47, which is tied to +5 volts.

The base of Q8 is also attached to pin 5 of the charge pump U5, which acts as the motor speed controller 94 (FIG. 2) for the paper feed motor 90. Pin 4 of the charge pump U5 is tied to ground. Pin 3 of the charge pump U5 is attached to resistor R43 and capacitor C6, which are connected in parallel, while pin 2 is attached to capacitor C12 and pin 1 is connected to capacitor C19 and resistor R40, which goes to the tachometer 84 (FIG. 3A and FIG. 2). R43, C6, C12 and C19 are all tied together to ground, as well as pin 8 of the charge pump U5 and resistor R22, to form a filter for the frequency coming from the tachometer 84. Pin 7 of the charge pump U5 is connected to R22, voltage regulators VR10 and VR11, and pin 13 (RB7) of U3, while pin 6 is tied to +5 volts. When RB7 goes high (+5 volts), the paper feed motor 90 is set to "full tilt," which means that the paper feed motor 90 runs at the highest speed set for the instrument 2 (see FIG. 2). The center pin of VR11 is connected to pin 12 (RB6) of U3, and the center pin of VR10 is connected to pin 11 (RB5) of U3. When RB6 goes high (+5 volts), the paper feed motor 90 is set to 25 mm/sec, and when RB5 goes high (+5 volts), the paper feed motor is set to 5 mm/sec. VR 10, VR11, and R22 are used as resistor dividers to divide the +5 volts from U3 to approximately +1 volt.

The tachometer 84 (FIG. 3A and FIG. 2), which determines the speed for the paper feed motor 90, is coupled to a motor speed regulator circuit. Specifically, pin 7 of the tachometer 84 is connected to resistor R40 and pin 6 is tied to ground. R40 is connected to the pin 7 of the charge pump U5 and to C19.

C14, which is connected to pin 1 of the pen heater 88 (FIG. 3A), is part of a voltage doubler network, which turns the battery voltage of +12 volts into +24 volts. C14 is attached to the head of diode D16, which has its tail tied to the +12 volt battery, and to the tail of diode D11, which is connected to capacitor C16 and voltage input (VI) of voltage regulator REG4. C14, C16, D16 and D11 for the voltage doubler network. C16 is connected to the +12 volt battery and capacitor C15, which is tied to ground. C15 is used to filter the small impedance from the +12 volt battery. Voltage output (VO) of REG4 sends out +12 volts filtered to the sensitive differential amps which have large gain (e.g., U1 and U2A). VO of REG4 is also attached to capacitor C22, which is tied to ground and acts as a stabilizing filter, while GND of REG4 is tied to ground.

Microcontroller U3 and corresponding components form the microcontroller circuit 92 (FIG. 2). Pin 1 (RA2) of U3, as described above, is an input which is connected to the cuff select switch SW1 (FIG. 3A). RA2 receives +5 volts when the wiper for SW1 changes positions to indicate a new cuff selection.

Pin 2 (RA3) of U3 is tied high to +5 volts through resistor R7 and to the first position of switch SW3 (FIG. 3C), which is connected to the power switch knob 10 (FIG. 1). The first position of the first pole of SW3 is "OFF", which represents no power to the instrument. The second position is "ON", which represents power to the instrument and either 5 mm/sec. or 25 mm/sec. paper feed motor speeds. The third position is "PAPER FEED", which is tied to ground, supplies power to the instrument like the "ON" position and additionally sends a signal to the microcontroller indicating that the chart recorder should run at "full tilt" speed.

Pin 3 (RTCC) and pin 4 (MCLR) of U3 are both tied high to +5 volts. Pin 5 (GND) of U3 is tied to ground.

Pin 6 (RB0) is an output which is connected to an "auto zero" circuit 94 (FIG. 2). Referring to FIG. 3B, RB0 is connected to resistor R42 (FIG. 3A), which is attached to the base of transistor Q5. The collector of Q5 is connected to +12 volts filtered through resistor R41 and switch SW4, while the emitter of Q5 is tied to ground. When the cuff selection is changed, a +5 volt pulse is sent to the "auto zero" circuit 94, and the "auto zero" circuit 94 closes U4A, U4B, U4C and U4D. When closed, U4A, U4B, U4C and U4D connect the "auto zero" pulse to R69, R23, the output of U6A, the "+" terminal of U6C, and the "+" terminal of U6D. Therefore, when U4A, U4B, U4C and U4D close, they switch from an open to a ground, and a zero (ground) pulse is sent to U1, U6A, U6C and U6D.

Referring to FIG. 3D, pin 6 (RB1), pin 7 (RB2) and pin 8 (RB3) of U3 are outputs. These pins generate the modulated pulse for the pen heater 88 (FIG. 2).

Pin 10 (RB4) is an output tied to the head of a LED D2, with the tail of LED 8 connected to +5 volts through resistor R38. The light for LED D2 is shown as indicator 8 in FIG. 1. RB4 sends a constant voltage to LED D2 when the power is "on", which causes the light from indicator 8 to be constant. On the other hand, RB4 sends a pulse modulated voltage to LED D2 when the power is "low", which causes the light from indicator 8 to flash.

Pin 11 (RB5), pin 12 (RB6) and pin 13 (RB7) are outputs which control the speed of the paper feed motor 90 (FIG. 2), as described above. Pin 14 (V+) is an input which powers U3 and is tied high to +5 volts, and pin 15 (OSC2/OUT) floats. Pin 16 (OSC1), which allows an oscillating clock to run on U3, is coupled to +5 volts through resistor R48 and ground through capacitor C13 such that the oscillating clocks runs at approximately 4 MegaHertz.

Pin 17 (RA0) of U3 is an input which is connected to footswitch circuitry 48. Specifically, RA0 is attached to resistor R39, which is tied to +5 volts through resistor R8 and is connected to the footswitch 48 (FIG. 2). When the footswitch 48 is activated, a pulse is sent to RA0 to activate the instrument 2 (FIG. 1).

Pin 18 (RA1) of U3 is an input which senses when power to the instrument 2 is low. RA1 is connected to ground through resistor R13 and is attached to the battery voltage sensor circuitry 93 through the collector of transistor Q1. The base of Q1 is tied to +5 volts, and the emitter of Q1 is attached to the center pin of potentiometer VR2. One side of VR2 is coupled to the +12 volt battery through resistor R9, and the other side is tied to ground through resistor R10. The power sensing circuit indicates "low" power when the voltage gets below +11.2 volts indicating that approximately only 20% of the battery is unused.

Referring to FIG. 3C, voltage regulators REG1 and REG2 produce +8 volts and +5 volts, respectively. The +12 volt battery is connected to the voltage input (VI) of REG1 through resistor R55 and to the voltage input (VI) of REG2. VI of REG2 is also connected to capacitor C9, which is tied to ground and to capacitor C8. The voltage output (VO) of REG1 is connected to C8 and outputs +8 volts, and the ground pin (GND) of REG1 is tied to ground. The voltage output (VO) of REG2 is connected to capacitor C7, which is tied to ground, and outputs +5 volts, while the ground pin (GND) of REG2 is tied to ground.

The +12 volt battery preferably handles 4 amps per hour. The battery is attached to the second pole of SW3 through a 1 amp slo-blo fuse 22 (FIG. 1), and directly to the third pole of SW3. The second and third positions of the second pole of SW3 are the output pins for the +12 volt battery. The first pin of the second pole of SW3 is connected to the head of diode D1, which is the output of the battery charger circuit. D1 allows current to travel only in the charging direction, not the discharging direction. The tail of D1 is attached to the voltage output (VO) of voltage regulator REG3, resistor R56, capacitor C20, and resistor R58. R56 is connected to the ground (GND) of REG3, resistor R57, and the collector of transistor Q4. The voltage input (VI) of REG3 is attached to the heads of diodes D15 and D14, as well as capacitor C18. REG3 and the surrounding circuitry is used to charge the battery up to +14.2 volts.

R58 is connected to the tail of LED D3, which is shown as indicator 18 in FIG. 1 as the battery charge indicator. The head of D3 is attached to the first position of pole three of SW3, as well as C20, and the center pin of potentiometer VR3. VR3 is connected to R57 and is used to adjust REG3 to +14.2 volts. The head of D3 is also attached to resistors R15, R50, R49 and R51. R50, R49 and R51 are connected in parallel to the emitter of Q4, to C18, and to the tails of diodes D12 and D13. LED D3 is illuminated when the charging circuit is activated, which takes place only when the power select knob 10 is in the "off" position and a 16 volt AC power pack is plugged into the circuit. R15 is attached to the base of Q4. R15, R50, R49 and R51 form a current limiting circuit to limit the current charging the battery to 750 milliamps.

D15 is connected to D12 and jack J1 for 16 volts AC, while D14 is attached to D13 and the first position of pole four of SW3. D15, D14, D13 and D12 form a rectifier, and C18 acts as a filter. The other end of jack J1 for the 16 volts AC is attached to the third position of the fourth pole of SW3. The second and third positions of the third pole of SW3 are tied to ground, and the second position of the fourth pole of SW3 is left floating.

Set forth below is table I, which lists component values and types which are used in a presently preferred embodiment of the circuit illustrated in FIGS. 3A–3D. As one of ordinary skill in the art would readily recognize, equivalent component values and parts may be substituted for the components listed in table I.

TABLE I

| COMPONENTS | VALUE/PART |
| --- | --- |
| R1, R2, R3, R4, R5, R6, R7, R8, R9, R10 | 10K |
| VR1 | 10K |
| VR2 | 10K |
| C1, C17, C21 | .01uF |
| R11, R12, R13, R69 | 1M |
| PT1 | FPM-05PG |
| U1 | LF411 |
| C2, C10, C11 | .1uF |
| R14, R52, R53 | 150K |
| D1, D4, D5, D6, D7, D8, D9, D10, D11, D12, D13, D14, D15, D16 | IN4001 |
| Q1, Q2, Q3 | 2N3906 |
| D2, D3 | LED |
| SW1 | SP6T |
| SW2 | DP6T |
| R15, R16, R17, R56 | 200 |
| Q4, Q5, Q6, Q7, Q8, Q9 | 2N3904 |
| R18, R19, R20, R21, R22, R58, R65, R67 | 1K |
| VR3, VR4 | 1K |
| R23 | 6.8K |
| R24 | 10.0K 1% |
| R25 | 24.9K 1% |
| R26 | 49.9K 1% |
| R27 | 332K 1% |
| R28 | 1.00M 1% |
| R29, R59, R60, R61, R62 | 100K 1% |
| U2, U6 | LM324 |
| REG1 | 78L08 |
| R30, R31, R63 | 20K |
| C3, C4, C5, C6 | 1uF |
| VR5, VR6 | 100 |
| R32 | 100 |
| REG2 | 78L05 |
| U3 | PIC16C54 |
| U4 | 4066C |
| Q10, Q11 | TIP42 |
| Q12, Q13, Q14, Q15 | TIP41 |
| R33 | 390 |
| R34 | 30K |
| R35, R36, R37, R44, R45, R55 | 11 |
| REG3 | LM317 |
| R38 | 300 |
| R39, R40, R41, R42 | 100K |
| VR7, VR8, VR9 | 100K |
| VR10, VR11 | 100K |
| C7, C8, C9, C22 | 100uF |
| C12 | .033uF |
| R43 | 47K |
| R46 | 820 |
| R47 | 430 |
| U5 | LM2907N-8 |
| C13 | 22pF |
| R48 | 4.7K |
| C14, C15, C16 | 470uF |
| REG4 | 78L12 |
| R49, R50, R51 | 2.7 |
| R54 | 82K |
| SW3 | SW 4P3T |
| R57, R68 | 2K |
| C18 | 1000uF |
| C19 | .1uF |
| C20 | 100uF |
| R64, R66 | 3K |
| U10 | FPM-05PG |
| J1 | Standard Mini Jack |

Figure 4:
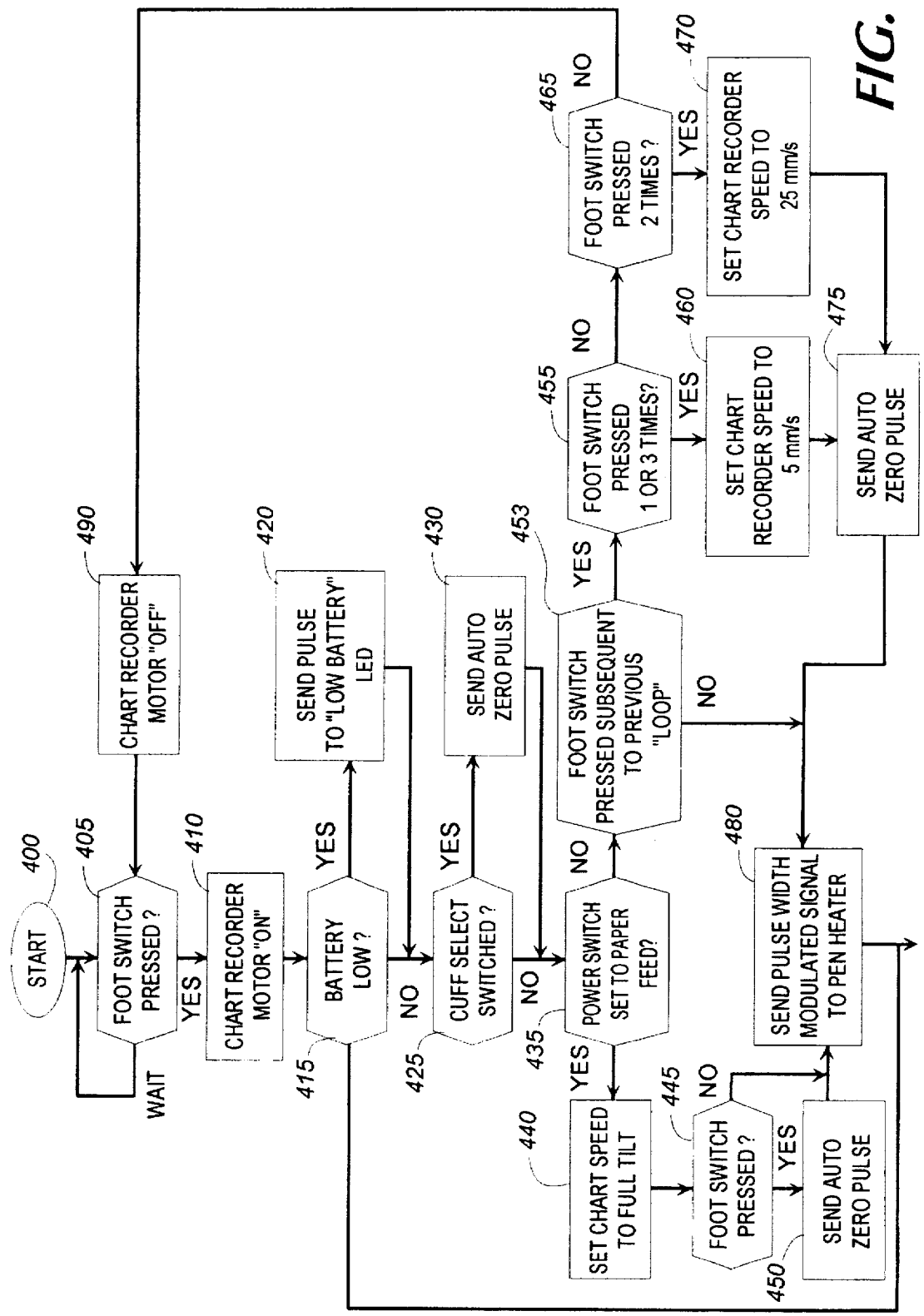
FIG. 4 is a flow chart showing the operation of the microcontroller illustrated in FIGS. 2 and 3D of the pressure measurement device according to the present invention.

FIG. 4 is a flow chart which illustrates the decision making process of the microcontroller circuit 92 (FIG. 2) and more specifically the microcontroller U3 (FIG. 30) in a presently preferred embodiment. The code for the microcontroller is preferably written such that all functions in the "loop" are cycled through approximately every 150 us when the instrument is activated. The "loop" is defined as block 415 to block 480 and back to block 415, as described in more detail below.

At block 400, power to the instrument 2 (FIG. 1) is turned on. The microcontroller then proceeds to decision block 405 to determine when the footswitch 48 (FIG. 1) has been pressed. As long as the footswitch is not pressed, the microcontroller waits at decision block 405.

After the footswitch 48 is pressed, the microcontroller proceeds to block 410. At block 410, the microcontroller sends a signal to turn the chart recorder "on."

The microcontroller then proceeds to the beginning of the "loop." The "loop" starts at decision block 415, where the microcontroller determines whether the battery for the instrument is low.

If the battery is low, then the microcontroller proceeds to block 420. At block 420, the microcontroller sends a pulse to light the "LOW BATTERY" indicator 8 (FIG. 1). The microcontroller then proceeds from block 420 to decision block 425. If the battery is not low, then the microcontroller proceeds directly from block 415 to decision block 425.

At decision block 425, the microcontroller determines whether the cuff selection knob 12 (FIG. 1) has been switched (e.g., from "1" to "2"). If the cuff selection knob 12 has been switched, then the microcontroller proceeds to block 430. At block 430, the microcontroller sends an auto zero pulse, which basically restarts the galvometer circuitry (FIGS. 3A–3D) to zero. The microcontroller then proceeds from block 430 to decision block 435. If the cuff selection knob 12 has not been switched, then the microcontroller proceeds directly from block 425 to decision block 435.

At decision block 435, the microcontroller determines whether the power switch knob 10 (FIG. 1) is set to "Paper Feed." If the power switch knob 10 is set to "Paper Feed," then the microcontroller proceeds to block 440, where the microcontroller sets the chart recorder 50 (FIG. 1) speed to "full tilt." The microcontroller, then proceeds to block 445 to determine whether the footswitch 48 has been pressed.

At block 445, if the footswitch 48 has been pressed, then the microcontroller proceeds to block 450. At block 450, the microcontroller sends an auto zero pulse to restart the galvometer circuitry (FIGS. 3A–3D). The microcontroller then proceeds from block 450 to block 480. If the footswitch 48 has not been pressed, then the microcontroller proceeds directly from block 445 to block 480.

Returning to block 435, if the microcontroller determines that the power switch knob 10 is not set to "Paper Feed," the microcontroller proceeds to decision block 453. At decision block 453, the microcontroller determines whether the footswitch 48 has been pressed subsequent to the previous "loop." If the footswitch 48 has not been pressed, then the microcontroller proceeds directly to block 480. However, if the footswitch 48 has been pressed, then the microcontroller proceeds to decision block 455.

At decision block 455, the microcontroller determines whether the footswitch 48 has been pressed one or three times. If the footswitch 48 has been pressed one or three times, then the microcontroller proceeds to block 460 where the chart recorder speed is set to 5 mm/s. From block 460, the microcontroller then proceeds to block 475.

Returning to block 455, if the microcontroller determines that the footswitch 48 has not been pressed one or three times, then the microcontroller proceeds to decision block 465. At decision block 465, the microcontroller determines whether the footswitch 48 has been pressed two times. If the footswitch 48 has been pressed two times, then the microcontroller proceeds to block 470, where the chart recorder speed is set to 25 mm/s. From block 470, the microcontroller proceeds to block 475.

At block 475, the microcontroller sends an auto zero pulse to restart the galvometer circuitry (FIGS. 3A–3D). The microcontroller then proceeds from block 475 to block 480.

At block 480, the microcontroller sends a pulse width modulated signal to the pen heater 88 (FIG. 2). The microcontroller then proceeds to decision block 415 to repeat the "loop" until the user of the instrument 2 is ready to turn it off.

Returning to decision block 465, when the user is ready to turn the chart recorder 52 (FIG. 2) off, the user will have pressed the footswitch 48 four times. Therefore, the microcontroller will determine that the footswitch has not been pressed two times at decision block 465 and proceed to block 490.

At block 490, the microcontroller turns the motor to the chart recorder 52 "off." The microcontroller then proceeds to decision block 405 to determine when the footswitch 48 is pressed again to turn the chart recorder 52 back "on" and begin the "loop" again.

Figure 5:
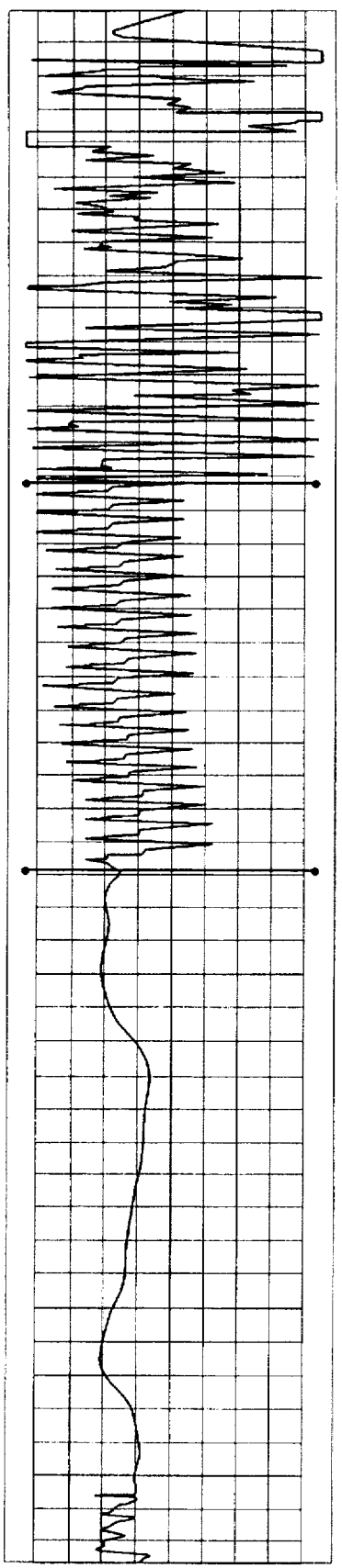
FIG. 5 is an example of a specific wave form plotted by the pressure measurement device according to the present invention.

FIG. 5 illustrates a possible wave form plotted by the pressure measurement device of the present invention. The wave form may then be analyzed by a physician to determine possible abnormalities or disorders in a patient.

It should be understood that various changes to the present invention may be made by the ordinarily skilled artisan, without departing from the spirit and scope of the present invention which is presented in the claims below. The ordinarily skilled artisan will understand that this disclosure presents an example of the invention and is not meant to limit the invention, as presented in the claims, in any way whatsoever.

I claim:

1. A method for vascular testing for diagnosing circulatory and secondary nervous disorders comprising the steps of:

providing a vascular testing device having a plurality of pneumatic cuffs;

fitting each of said pneumatic cuffs over separate body extremities;

pressurizing each of said pneumatic cuffs to an initial pressure and maintaining said pressure in each of said cuffs for a predetermined period sufficient to monitor a volume of blood flow in said extremity;

monitoring an internal pressure of a respective of said cuff resulting from blood flowing from said extremity while maintaining pressure in each of said respective cuffs;

sensing pressure fluctuations within a respective of said cuff resulting from blood flowing through said extremity;

producing an electrical signal representing the pressure fluctuations within a respective of said selective pneumatic cuffs;

displaying data corresponding to said pressure fluctuations representing the volumetric flow of blood through said extremity;

repeating steps d through g for each respective extremity until the blood flow through all monitored extremities has been monitored; and comparing the volumetric flow of blood from each extremity for diagnosing circular or secondary nervous disorders.

2. The method of claim 1 further comprising the step of selecting one pneumatic cuff from said plurality of pneumatic cuffs for sensing the pressure fluctuations within that respective cuff wherein said pressure fluctuation results from blood flowing through said extremity.

3. The method of claim 1 wherein said method further includes placing said plurality of pneumatic cuffs over fingers of an individual.

4. The method of claim 1 wherein said pneumatic cuffs are simultaneously inflated to a predetermined pressure from a pressure source.

5. The method of claim 1 wherein data corresponding to each pneumatic cuff represents the pressure fluctuation within each cuff resulting from the volumetric flow of blood through a corresponding extremity as displayed by said display.

* * * * *